(12) United States Patent  (10) Patent No.: US 7,379,524 B2
Bair  (45) Date of Patent: May 27, 2008

(54) COMPUTER TOMOGRAPHY SCANNER

(75) Inventor: Nathaniel Bair, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 375 days.

(21) Appl. No.: 10/662,500

(22) Filed: Sep. 15, 2003

(65) Prior Publication Data

US 2004/0062357 A1   Apr. 1, 2004

Related U.S. Application Data

(60) Provisional application No. 60/410,847, filed on Sep. 13, 2002.

(51) Int. Cl.
*A61B 6/00* (2006.01)
(52) U.S. Cl. ............................. 378/4; 378/38
(58) Field of Classification Search .............. 378/4–20, 378/38–40, 193–197
See application file for complete search history.

(56) References Cited

U.S. PATENT DOCUMENTS

| 5,469,488 | A | 11/1995 | Ono |
| 5,677,940 | A * | 10/1997 | Suzuki et al. ................. 378/38 |
| 6,173,029 | B1 | 1/2001 | Xie et al. |
| 6,364,526 | B2 | 4/2002 | Ivan et al. |
| 6,389,104 | B1 | 5/2002 | Bani-Hashemi et al. |
| 6,426,992 | B1 | 7/2002 | Kohler et al. |
| 6,449,331 | B1 | 9/2002 | Nutt et al. |
| 6,459,756 | B1 | 10/2002 | Tam et al. |
| 6,480,565 | B1 * | 11/2002 | Ning ........................... 378/37 |
| 6,490,334 | B1 | 12/2002 | Wang et al. |
| 6,496,558 | B2 * | 12/2002 | Graumann ................... 378/39 |
| 2001/0021244 | A1 * | 9/2001 | Suzuki et al. ............... 378/196 |

FOREIGN PATENT DOCUMENTS

WO   WO 9917659 A1 *   4/1999

* cited by examiner

*Primary Examiner*—Courtney Thomas
(74) *Attorney, Agent, or Firm*—Carlson, Gaskey & Olds

(57) ABSTRACT

A CT scanner includes a gantry supporting an x-ray source and an x-ray detector. A motor in the gantry controls rotation of the gantry relative to a mounting plate from which the gantry is supported. The gantry also houses a computer for controlling the motor to rotate the gantry in a controlled, known manner. The computer also controls the x-ray source, including powering the x-ray source on and off and varying the intensity and frequency of the produced x-ray. The computer also collects data from the x-ray detector.

38 Claims, 1 Drawing Sheet

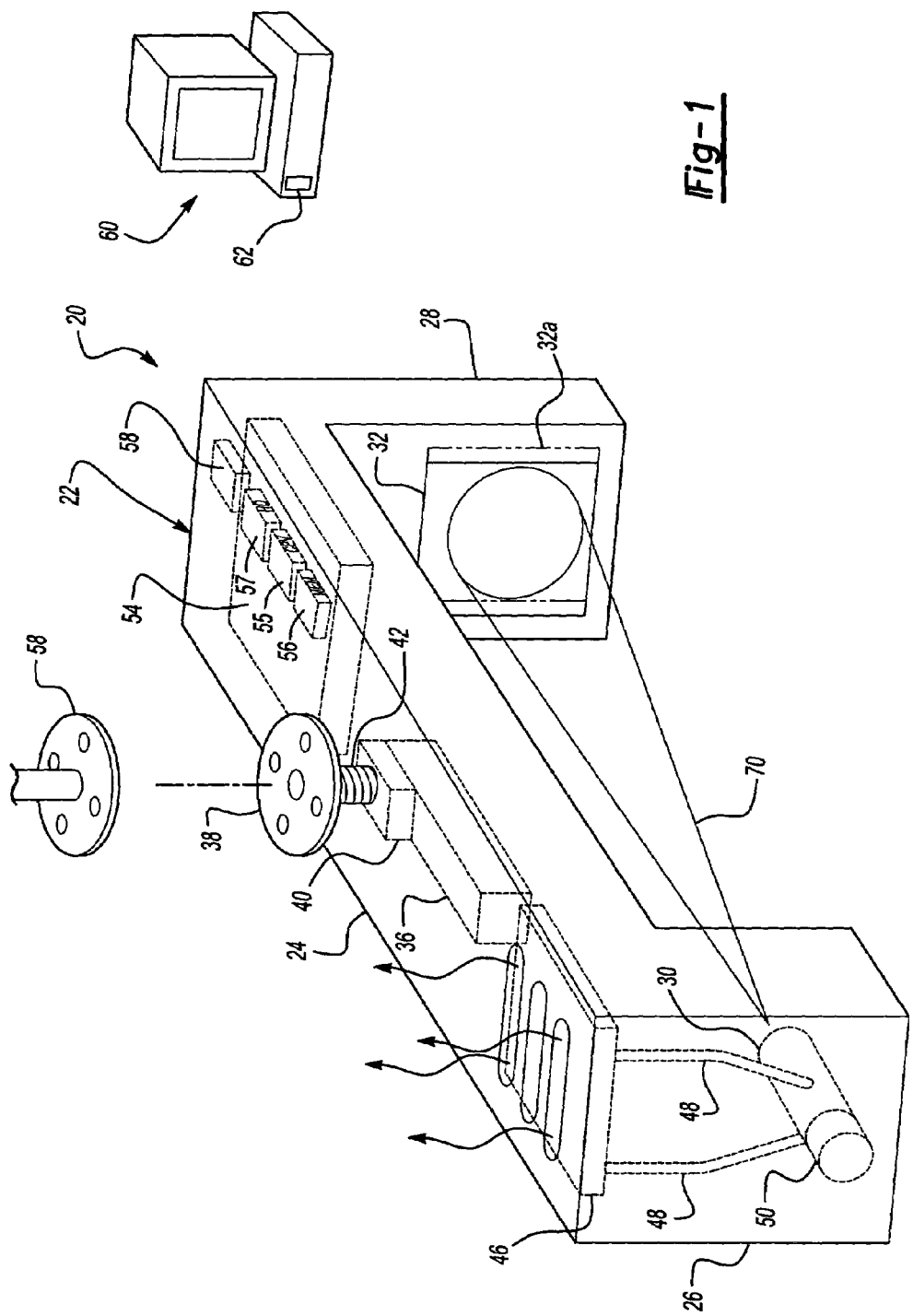

COMPUTER TOMOGRAPHY SCANNER

This application claims priority to U.S. Provisional Application Ser. No. 60/410,847, filed Sep. 13, 2002.

BACKGROUND OF THE INVENTION

The present invention relates generally to computer tomography (CT) scanners and more particularly to a more compact CT scanner. Generally, computer tomography scanners are large enough to scan a patient's entire body. Typically, an x-ray source is mounted on a movable ring, which also includes an array of x-ray detectors opposite the x-ray source. The patient lies on a platform that moves through the ring. The ring is rotated so the x-ray source and detectors revolve around the patient, while the patient is moved through the ring on the platform. The x-ray slices through the body by taking a series of x-rays in a spiral pattern. The x-ray source is typically a "fan beam" x-ray source, i.e., it sends a fan-shaped beam that defines a single plane through the body and is received by the detectors.

These scanners are very large because they are capable of scanning an entire body and must include a platform movable through the x-ray source and detectors. An entire room is often dedicated to such a scanner and its associated equipment.

Because the scanner takes only narrow slices through the body, the x-ray source and detectors must make numerous revolutions just to scan a small area of the body. Further, because some of the internal organs that are being scanned may move, it is important that the scanner and detectors revolve very quickly and process the information very quickly. This greatly increases the cost and complexity of the current design.

SUMMARY OF THE INVENTION

The present invention provides a smaller, self-contained, lower cost CT scanner. The scanner includes a gantry on which the x-ray source and x-ray detector are mounted. A motor in the gantry controls rotation of the gantry relative to a mounting plate from which the gantry is supported. The gantry also houses a computer for controlling the motor to rotate the gantry in a controlled, known manner. The computer also controls the x-ray source, including powering the x-ray source on and off and varying the intensity and frequency of the produced x-ray. The computer also collects data from the x-ray detector. The computer may also generate a three-dimensional model based upon the collected images.

BRIEF DESCRIPTION OF THE DRAWINGS

Other advantages of the present invention can be understood by reference to the following detailed description when considered in connection with the accompanying drawings wherein:

FIG. 1 is a schematic view of a CT scanner according to the present invention.

DETAILED DESCRIPTION OF THE PREFERRED EMBODIMENTS

A CT scanner 20 according to the present invention is illustrated in FIG. 1. In the CT scanner 20, all of the components are contained in a gantry 22. The gantry 22 provides the structural support and the housing for the components. The gantry 22 comprises a cross-bar section 24 from which a first arm 26 and a second arm 28 extend perpendicularly from either end.

The first arm 26 houses the x-ray source 30, which in this embodiment is a cone-beam x-ray source 30. The second arm 28 houses a complementary detector 32. The detector 32 is a two-dimensional detector as shown. The detector 32 is optionally selectively movable in a direction perpendicular to the second arm 28 and perpendicular to the axis of the x-ray beam to a position indicated in phantom as detector 32a. The detector 32 may be movable up to approximately 3 inches.

The cross-bar section 24 of the gantry 22 houses a motor 36 for rotating the gantry 22 relative to a mounting plate 38. The motor 36 may directly drive the mounting plate 38, or a gear box 40 may be provided between the motor 36 and mounting plate 38. As an additional option, a ball screw 42 may be provided between the motor 36 and mounting plate 38 for providing some translation of the gantry 22 along the axis of rotation of the motor 36. For example, the ball screw 42 would provide approximately 1 inch of translation (vertically in FIG. 1) in one complete rotation of the gantry 22.

The gantry 22 further includes a heat exchanger 46 for cooling the x-ray source 30. The heat exchanger 46 contains cooling oil circulated to and from the x-ray source 30 via lines 48. The cooling oil brings heat from the x-ray source 30 to the heat exchanger 46 for dissipation. The heat exchanger 46 may also include a fan (not shown) for cooling the cooling oil. As an alternative to or in addition to the heat exchanger 46, the CT scanner 20 may include a piezoelectric cooling system 50 (shown in phantom) for cooling the x-ray source 30.

The CT scanner 22 further includes an on-board computer 54 including a microprocessor or CPU 55, memory 56, a hard drive 57 and/or other optical, magnetic, electronic or other mass storage, and other hardware and software for performing the functions described herein. Note that for simplicity all connections between the computer 54 and the other components in the CT scanner 20 are not shown. The processor 54 in the disclosed embodiment performs at least these three functions: First, the computer 54 controls the rotation of the CT scanner 20 by controlling the motor 36. Second, the computer 54 also controls the x-ray source 30, including powering the source 30 on and off and varying the intensity of the produced x-ray. Third, the computer 54 collects the data from the detector 32 and stores it for later collection, such as in memory 56 or storage 57. If the detector 32 is movable to the position shown as detector 32a, the computer 43 also controls the movement and position of the detector 32 relative to the arm 28, via a motor or other means.

The computer 54 includes a wireless transmitter 58 for transmitting the data after collection to an off-board computer 60 that includes a complementary wireless receiver 62. The off-board computer 60 processes the data collected by the CT scanner 20 to create the 3D models and images. Optionally, the computer 54 could be connected via traditional wires or optical connections to the computer 60. Communication and power may be provided to the CT scanner 20 through wires (not shown) passing through mounting plates 38 and 58.

Optionally, the on-board computer 54 may also process the data from the detector 32, including building the 3-D model or image of what was scanned. The 3-D model would be stored in memory 56 and/or storage 57 before being transmitted to off-board computer 60.

Installation of the CT scanner 20 of the present invention is greatly simplified. Because the CT scanner 20 is completely self-contained within the gantry 22, the CT scanner 20 is manufactured, assembled, tested and calibrated off-site. Installation only requires mounting the mounting plate 58 to the ceiling and securing the CT scanner 20 to the mounting plate 58. As another feature of the present invention, the CT scanner 20 could also be mounted to a mounting plate 58 extending horizontally from a wall, such that the axis of rotation is horizontal, such as for scanning a portion of a body of a patient who is lying down. Further, because the CT scanner 20 is small, it could also be mounted on a multiple axis arm, such that the CT scanner 20 could be positioned and oriented as desired for the convenience of the patient.

In operation, the part of the body to be scanned is positioned between the first arm 26 and the second arm 28 of the gantry 22. The computer 54 powers on the x-ray source 30. The x-ray source 30 generates a cone-beam x-ray 70 that is directed toward the detector 32. The processor 54 then controls the motor 36 to perform one complete revolution of the gantry 22, during which time the computer 54 collects multiple images from the detector 32. With the optional ball screw 42, during the single revolution, the CT scanner 20 also translates approximately 1 inch along the axis of rotation, thus providing additional data for the computer 54. The images taken by detector 32 are stored in memory 56 and/or storage 57.

The data collected by the computer 54 is then transmitted via transmitter 58 to the receiver 62 and collected by the computer 60. The computer 60 then generates the 3-D models or images of the scanned body part based upon the data. Since the images are stored on-board the CT scanner 20 at least temporarily, they can be transmitted to the off-board computer 60 at a slower rate. Whether the on-board computer 54 generates the 3-D models or simply stores the images, the wireless transmitter 58 does not need to transmit the images in real time, which would probably require a higher bandwidth than currently available for currently-available low-cost wireless transmitters 58. Alternatively, since the images (or the 3-D model) are stored temporarily on the CT scanner 20, a wire (such as an Ethernet cable) can be connected between the on-board computer 54 and the off-board computer 60 after the CT scanner 20 completes the scanning process, when the CT scanner 20 is no longer rotating.

The CT scanner 20 gathers more information in each image with the cone-beam x-ray source 30. Because only a portion of the body is being scanned by the cone-beam x-ray source 30, only a single revolution is required. The present invention is not required to rotate as quickly as the prior art fan-beam CT scanners because more data is being collected at one time and because only one revolution is required. The rotation rate can further be reduced if the CT scanner 20 is intended to be used only for body parts that would not move during the single revolution, such as the head, or the arms or legs, as opposed to internal organs that move involuntarily. This greatly reduces the cost and complexity of this design. As demonstrated above, the CT scanner 20 of the present invention is compact, self-contained and lower cost than known CT scanners.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope.

Alphanumeric labels on method steps are for ease of reference in dependent claims and unless otherwise specified do not require a specific sequence in which the steps are to be performed.

What is claimed is:

1. A computed tomography scanner comprising:
   a gantry;
   an x-ray source mounted to the gantry;
   an x-ray detector mounted to the gantry opposite the x-ray source; and
   a motor fixed to the gantry, such that the motor rotates with the gantry.

2. The computed tomography scanner according to claim 1 further including a mounting plate secured to the motor, such that the motor imparts relative rotation between the mounting plate and the gantry.

3. The computed tomography scanner of claim 2 wherein the mounting plate rotates relative to the motor and gantry.

4. The computed tomography scanner of claim 3 wherein the motor also imparts translational movement of the gantry relative to the mounting plate.

5. The computed tomography scanner according to claim 1 further including a computer mounted to the gantry, such that the computer rotates with the gantry.

6. The computed tomography scanner according to claim 5 wherein the computer sends signals the motor to control the rotation of the gantry.

7. The computed tomography scanner of claim 5 wherein the computer controls the x-ray source.

8. The computed tomography scanner of claim 5 wherein the computer controls movement of the x-ray detector relative to the gantry.

9. The computed tomography scanner of claim 5 wherein the computer processes images collected from the x-ray detector.

10. The computed tomography scanner of claim 9 wherein the computer creates a three-dimensional model based upon the images collected from the x-ray detector.

11. The computed tomography scanner of claim 1 wherein the x-ray detector is movable relative to the gantry.

12. The computed tomography scanner of claim 1 wherein the gantry includes a housing in which the x-ray source is at least partially mounted.

13. The computed tomography scanner of claim 1 wherein the x-ray source is a cone-beam x-ray source.

14. A computed tomography scanner comprising:
    a gantry including a cross bar;
    an x-ray source mounted to the gantry vertically downward of the cross bar;
    an x-ray detector mounted to the gantry vertically downward of the cross bar and positioned horizontally opposite the x-ray source;
    a mount rotatable relative to the gantry; and
    a computer mounted to the gantry, the computer movable with the gantry relative to the mount.

15. The computed tomography scanner of claim 14 wherein the computer controls the x-ray source.

16. The computed tomography scanner of claim 14 wherein the computer controls movement of the x-ray detector relative to the gantry.

17. The computed tomography scanner of claim 14 wherein the computer processes images collected from the x-ray detector.

18. The computed tomography scanner of claim 17 wherein the computer creates a three-dimensional model based upon the images collected from the x-ray detector.

19. The computed tomography scanner of claim 18 further including a wireless transmitter on the gantry, the transmitter transmitting the three-dimensional model from the computer.

20. The computed tomography scanner of claim 14 wherein the mount is positioned vertically above the cross bar.

21. The computed tomography scanner of claim 20 wherein the gantry is suspended vertically downward from the mount.

22. The computed tomography scanner of claim 14 wherein the source and the detector are suspended from the cross bar.

23. A computed tomography scanner comprising:
   a gantry;
   an x-ray source mounted to the gantry;
   an x-ray detector mounted to the gantry opposite the x-ray source;
   a mount rotatably mounted to the gantry;
   a motor mounted to at least one of the gantry and the mount, the motor selectively imparting relative motion between the mount and the gantry; and
   a computer mounted to the gantry such that the computer rotates with the gantry, the computer controlling rotation of the gantry relative to the mount by the motor, the computer controlling the x-ray source.

24. The computed tomography scanner of claim 23 wherein the computer processes images collected from the x-ray detector.

25. The computed tomography scanner of claim 24 wherein the computer creates a three-dimensional model based upon the images collected from the x-ray detector.

26. The computed tomography scanner of claim 25 further including a wireless transmitter on the gantry, the transmitter transmitting the three-dimensional model from the computer.

27. A method for imaging a portion of a body including the steps of:
   a) positioning the body part between a source and a detector and below a cross bar connecting the source and the detector;
   b) revolving the source and the detector about the body part;
   c) taking a series of images from the detector from a plurality of positions about the body part during step b); and
   d) storing the series of images in a first location revolving with the detector in step b).

28. The method of claim 27 further including the step of:
   e) transmitting the series of images stored in said step d) after said steps a-d) to an off-board storage.

29. The method of claim 27 further including the step of:
   e) generating a three-dimensional model of the body part from the series of images.

30. The method of claim 29 wherein said step e) is performed at a second location revolving with the detector in step b).

31. The method of claim 30 further including the step of:
   f) transmitting the three-dimensional model to an off-board storage.

32. The method of claim 31 wherein said step f) includes the step of transmitting the three-dimensional model wirelessly.

33. The method of claim 29 wherein only a single complete revolution is performed in said step b) before the three-dimensional model is performed in said step e).

34. The method of claim 29 further including the step of translating the source and the detector about an axis of the revolution during said step b).

35. The method of claim 27 wherein the body part is positioned below a horizontal plane containing the cross bar in said step a).

36. The method of claim 27 wherein said step b) further includes the step of rotating the source and the detector relative to a mount positioned above the cross bar and connected to the cross bar.

37. The method of claim 36 further including the step of:
   e) prior to said step a), hanging the cross bar, the source and the detector from the mount.

38. The method of claim 37 wherein the cross bar, the source and the detector hang vertically downwardly from the mount after said step e).

* * * * *